United States Patent [19]

Gadient

[11] Patent Number: 4,673,674
[45] Date of Patent: Jun. 16, 1987

[54] DIAZEPINOINDOLES USEFUL FOR TREATING DEPRESSION, SCHIZOPHRENIA, SOCIAL WITHDRAWAL OR ANXIETY AND PHARMACEUTICAL COMPOSITIONS CONTAINING THEM

[75] Inventor: Fulvio Gadient, Birsfelden, Switzerland

[73] Assignee: Sandoz Pharmaceuticals Corp., E. Hanover, N.J.

[21] Appl. No.: 704,040

[22] Filed: Feb. 21, 1985

[30] Foreign Application Priority Data

Feb. 22, 1984 [CH] Switzerland ............................ 863/84

[51] Int. Cl.$^4$ .................... C07D 487/04; A61K 31/40
[52] U.S. Cl. ..................................... 514/220; 540/561
[58] Field of Search ..................... 200/245.7; 540/561; 514/220

[56] References Cited

U.S. PATENT DOCUMENTS 4,210,590  7/1980  Maryanoff et al. ................. 540/561

FOREIGN PATENT DOCUMENTS 860049  4/1978  Belgium .
2120662  12/1983  United Kingdom ............ 260/245.7

OTHER PUBLICATIONS

Science, vol. 192, pp. 481–483 (1976).
Biochem. Pharm., vol. 27, pp. 307–316 (1978).
Amer. J. Psychiat., vol. 137, pp. 1518–1522 (1980).
Chem. Pharm. Bull., vol. 28, pp. 900–909 (1980).
Tetrahedron Letters No. 39, pp. 3399–3402 (1975).

*Primary Examiner*—Donald G. Daus
*Assistant Examiner*—William A. Teoli, Jr.
*Attorney, Agent, or Firm*—Gerald D. Sharkin; Robert S. Honor; Joseph J. Borovian

[57] ABSTRACT

Diazepinoindoles or pharmaceutically acceptable acid addition salts thereof are useful as antidepressant, conflict reducing or neuroleptic agents.

9 Claims, No Drawings

DIAZEPINOINDOLES USEFUL FOR TREATING DEPRESSION, SCHIZOPHRENIA, SOCIAL WITHDRAWAL OR ANXIETY AND PHARMACEUTICAL COMPOSITIONS CONTAINING THEM

The present invention relates to diazepinoindoles, their production and pharmaceutical compositions containing them.

In Chem. Pharm. Bull. 28 (1980) 900–909 the preparation of 4,5-dihydro-1H-[1,4]diazepino[1,7-a]indol-2(3H)-one as one of a number of by-products by photocyclisation of N-chloroacetyl-1-indolylethylamine is described. No utility for the compound is proposed.

The present invention provides 2,3,4,5-tetrahydro-1H-[1,4]diazepino-[1,7-a]indoles and acid addition salts thereof, hereinafter referred to as compounds of the invention. It is to be appreciated that the compounds of the invention may be optionally substituted in any available position. Preferred diazepinoindoles in accordance with the invention are those in which the 11-position is substituted by a phenyl group.

In particular the present invention provides a compound of formula I,

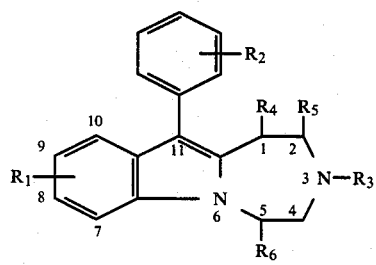

wherein
$R_1$ and $R_2$ are each, independently, hydrogen, halogen of atomic number from 9 to 35, $(C_{1-4})$alkyl, $(C_{1-4})$alkoxy or trifluoromethyl,
$R_3$ is hydrogen, $(C_{1-4})$alkyl, $(C_{3-6})$cycloalkyl, $(C_{3-6})$cycloalkyl$(C_{1-3})$ alkyl, $(C_{3-5})$alkenyl or $(C_{3-5})$alkynyl,
$R_4$, $R_5$ and $R_6$ are each, independently, hydrogen or $(C_{1-4})$alkyl, and acid addition salts thereof.

Any alkyl or alkoxy radical of 1 to 4 carbon atoms is preferably of 1 to 3 carbon atoms, especially 1 or 2 carbon atoms. Cycloalkyl or the cycloalkyl moiety of cycloalkylalkyl is conveniently cyclopentyl and especially cyclopropyl. The alkyl moiety of cycloalkylalkyl has conveniently 1 carbon atom. Halogen is preferably chlorine or fluorine and especially chlorine. The multiple bond of alkenyl or alkinyl is preferably not in the $\alpha,\beta$ position.

In formula I $R_1$ is preferably in position 8 or 9 of the nucleus. $R_2$ is preferably in position 2 or 4 of the phenyl ring.

The compounds of the invention which are substituted in the diazepine ring have one or more chiral centres. The compounds of formula I have one chiral centre when one of the substituents $R_4$, $R_5$ and $R_6$ is alkyl. The compounds contain further chiral centres, when further substituents are present. The compounds of the invention include all possible individual enantiomers, racemic mixtures, diastereoisomers as well as mixtures thereof.

The present invention in another aspect provides a process for the production of a compound of the invention which comprises (i) reducing a 2,3-dihydro-1H-[1,4]diazepino[1,7-a]indol-4(5H)-one or a 4,5-dihydro-1H-[1,4]diazepino[1,7-a]indol-2(3H)-one or an acid addition salt thereof, to a 2,3,4,5-tetrahydro-1H-[1,4]diazepino[1,7-a]indole or an acid addition salt thereof, (ii) converting a 2,3,4,5-tetrahydro-1H-[1,4]diazepino[1,7-a]indole substituted at the nitrogen atom in the 3 position or an acid addition salt thereof into a 2,3,4,5-tetrahydro-1H-[1,4]diazepino[1,7-a]indole unsubstituted at the nitrogen atom in the 3-position, or an acid addition salt thereof, and/or (iii) converting a 2,3,4,5-tetrahydro-1H-[1,4]diazepino[1,7-a]indole unsubstituted at the nitrogen atom in the 3-position or an acid addition salt thereof into a 2,3,4,5-tetrahydro-1H-[1,4]diazepino[1,7-a]indole substituted at the nitrogen atom in the 3-position, or an acid addition salt thereof, and recovering the compound of the invention in free base form or in acid addition salt form.

In particular a compound of formula I as defined above or an acid addition salt thereof may be produced by a process which comprises (a) producing a compound of formula Ia,

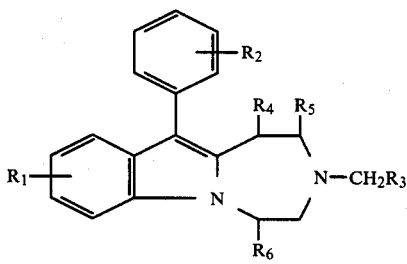

wherein $R_1$, $R_2$, $R_4$–$R_6$ are as defined above and $R_3'$ is hydrogen, $(C_{1-3})$alkyl, $(C_{3-6})$cycloalkyl or $(C_{3-6})$cycloalkyl$(C_{1-2})$alkyl, or an acid addition salt thereof, by reducing a compound of formula II,

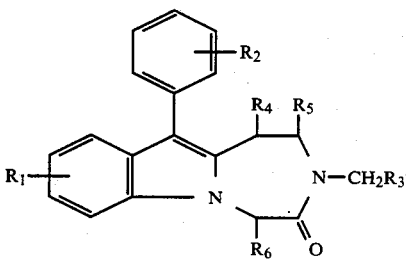

wherein $R_1$, $R_2$, $R_4$–$R_6$ and $R_3'$ are as defined above or an acid addition salt thereof or (b) producing a compound of formula Ib,

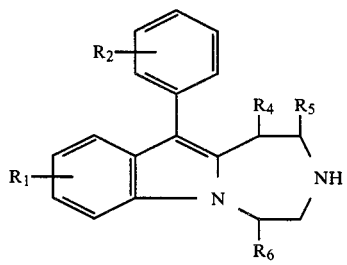

wherein $R_1$, $R_2$, $R_4$–$R_6$ are as defined above or an acid addition salt thereof, by demethylating a compound of formula Ia, wherein $R_3'$ is hydrogen, or an acid addition salt thereof, or (c) producing a compound of formula Ic, Ic

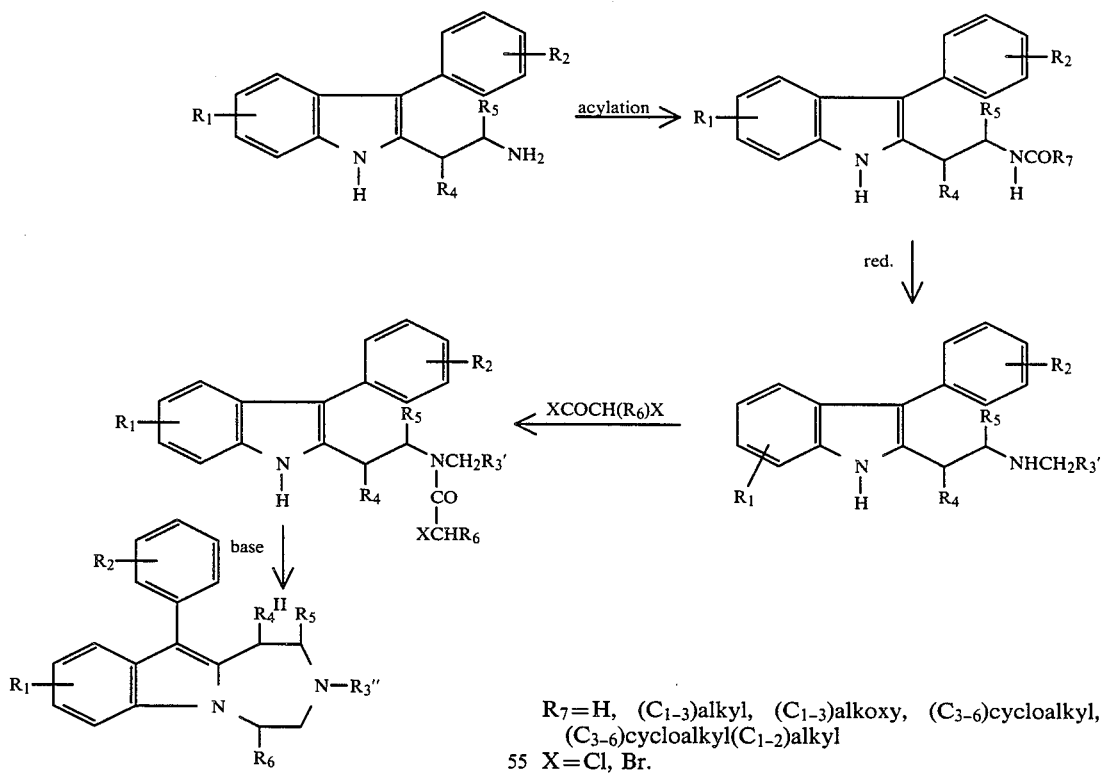

wherein $R_1$, $R_2$, $R_4$–$R_6$ are as defined above and $R_3''$ is $(C_{3-6})$cycloalkyl, $(C_{3-6})$cycloalkyl$(C_{1-3})$alkyl, $(C_{3-5})$alkenyl or $(C_{3-5})$alkynyl, or an acid addition salt thereof, by introducing the group $R_3''$ into a compound of formula Ib as defined above or an acid addition salt thereof, and recovering the compound of formula I in free base form or acid addition salt form.

Process (i) or (a) may be effected in conventional manner for analogous reductions. The reduction may be carried out with a complex hydride such as diborane, aluminium hydride or lithium aluminium hydride. Conveniently an inert organic solvent, e.g. an ether, such as tetrahydrofuran or dioxane, is used. Suitable temperatures may be from room temperature to the reflux temperature of the solvent.

Process (ii) or (b) may be effected in conventional manner. Demethylations may be carried out for example with haloformic acid esters, such as chloroformic acid ester, e.g. ethyl, phenyl, benzyl or vinyl ester.

Process (iii) or (c) may be effected in conventional manner for substitution of secondary amines. For example the process (c) may be an alkylation reaction. As an alkylation reaction it may be effected in conventional manner for the alkylation of an analogous secondary ring amine. The process may be carried out, e.g. using alkyl halides, or alkyl sulphates. Alternatively the N-alkyl derivatives may be obtained by reduction from the corresponding N-acyl-derivatives, which may be produced from a compound of formula Ib in conventional manner.

Naturally compounds of the invention may be converted into other compounds of the invention in conventional manner.

The starting material of formula II may be obtained for example as follows:

$R_7$=H, $(C_{1-3})$alkyl, $(C_{1-3})$alkoxy, $(C_{3-6})$cycloalkyl, $(C_{3-6})$cycloalkyl$(C_{1-2})$alkyl X=Cl, Br.

Insofar as the production of starting materials, e.g. 2,3-dihydro-3-alkyl-11-phenyl-diazepino[1,7-a]indol-4(5H)-ones other than those of formula II, is not particularly described these compounds may be produced in analogous manner to known compounds or to processes described herein.

Free base forms of the compounds of the invention may be converted into acid addition salt forms in conventional manner and vice versa. Suitable acids include, for example, hydrochloric acid, hydrobromic acid, maleic acid, fumaric acid and succinic acid.

A racemic mixture of the compounds of the invention may be resolved in known manner, for example using an optically active acid as a resolving agent. Alternatively, a pure enantiomeric or diastereoisomeric form may be produced by utilizing optically active respective diastereoisomeric starting materials.

In the following examples all temperatures are given in degrees Centigrade and are uncorrected.

In the Tables the following abbreviations are used:
(1) fumarate
(2) hydrogen fumarate
(3) hydrochloride
(4) isomer A (trans)
(5) isomer B (cis).

EXAMPLE 1

2,3,4,5-Tetrahydro-3-methyl-11-phenyl-1H-[1,4]diazepino[1,7-a]indole

[process (a)]

A solution of 26.7 ml sulphuric acid monohydrate in 267 ml tetrahydrofuran is added dropwise to a suspension of 37.8 g lithium aluminium hydride in 380 ml tetrahydrofuran at 0°. The mixture is stirred for 15 minutes at 0° then heated to 45° and treated dropwise with a suspension of 72.4 g 2,3-dihydro-3-methyl-11-phenyl-1H-[1,4]diazepino[1,7-a]indol-4(5H)-one in 725 ml tetrahydrofuran. After stirring for 2 ½ hours, the mixture is cooled to 0°. The mixture is treated dropwise with 133 ml saturated sodium sulfate solution followed by the addition of 66 ml 33% sodium hydroxide solution. Stirring is continued for 1 hour. The mixture is filtered and the residue washed with ether. The filtrate is evaporated under reduced pressure and the oily residue chromatographed on silica gel with methylene chloride, whereupon the title compound is obtained, m.p. 126°–128° (from ethanol).

The starting material may be obtained as follows (a) 3-Phenyl-1H-indol-2-ethanamine carbamic acid ethyl ester To a solution of 18.9 g 3-phenyl-1H-indol-2-ethanamine in 220 ml methylene chloride are added 15.3 ml of chloroformic ethyl ester followed by 110 ml water. The mixture is stirred for 10 minutes. 6.4 g sodium hydroxide in 100 ml water are added and stirring is continued for further 20 minutes at room temperature. The organic phase is separated, washed once with 2N tartaric acid and water, dried and evaporated under reduced pressure. The oily residue of the heading compound is used without further purification.

(b) N-Methyl-3-phenyl-1H-indol-2-ethanamine

A cold solution of 8.6 ml sulphuric acid monohydrate in 85.6 ml tetrahydrofuran is added dropwise to a suspension of 12.1 g lithium aluminium hydride in 243 ml tetrahydrofuran at 0°. The mixture is stirred at 0° for 15 minutes and treated at 0° to 10° dropwise with 24.6 g 3-phenyl-1H-indol-2-ethanamine carbamic acid ethyl ester in 274 ml tetrahydrofuran. The mixture is heated under reflux for 45 minutes, then cooled to 0° and treated dropwise with 43 ml of a saturated sodium sulfate solution. 21 ml of 30% sodium hydroxide solution are further added and the mixture stirred for 1 hour. The mixture is filtered and the residue washed with ether. The filtrate is evaporated under reduced pressure and the residue cristallised from ether/pentane to give the heading compound, m.p. 148°–151°.

(c) 2-Chloro-N-methyl-N-[2-(3-phenyl-1H-indol-2-yl)ethyl]acetamide

A solution of 17.5 ml chloroacetyl chloride in 100 ml chloroform is added dropwise within 15 minutes to a solution of 50.1 g N-methyl-3-phenyl-1H-indol-2-ethanamine and 30.7 ml triethylamine in 500 ml chloroform. After 30 minutes the mixture is made alkaline with aqueous ammonia. The organic phase is separated, washed with water and dried. Evaporation of the solvent gives the heading compound, m.p. 135°–138° (from methylene chloride/ether).

(d) 2,3-Dihydro-3-methyl-11-phenyl-1H-[1,4]diazepino[1,7-a]indol-4(5H)-one 7.9 g sodium hydride dispersion (55% in oil) are washed twice with pentane and suspended in 100 ml dimethylformamide. A solution of 49 g 2-chloro-N-methyl-N-[2-(3-phenyl-1H-indol-2-yl)ethyl]acetamide in 150 ml dimethylformamide is added dropwise within 15 minutes. The temperature rises to 50°. The mixture is stirred for 2 hours at room temperature, treated with ice-water and ethyl acetate. The organic phase is dried and the solvent evaporated to give the heading compound, m.p. 126°–128° (from ethanol).

EXAMPLE 2

2,3,4,5,-Tetrahydro-11-phenyl-1H-[1,4]diazepino[1,7-a]indole

[process (b)]

A solution of 23 ml chloroformic acid ethyl ester in 120 ml toluene is added dropwise to 44.2 g 2,3,4,5,-tetrahydro-3-methyl-11-phenyl-1H-[1,4]diazepino [1,7-a]indole and 41.3 ml N-ethyldiisopropyl amine in 320 ml toluene at 80°. The mixture is stirred for 2 hours at 80°. Water and acetic acid ethyl ester are added. The organic phase is washed with 2N hydrochloric acid and water, dried and evaporated. The oily residue is heated under reflux for 2 hours in a solution of 118.5 g potassium hydroxide in 790 ml 1-propanol. The mixture is poured into ice-water and extracted with methylene chloride. The organic phase is washed with water, dried and evaporated whereupon the title compound is obtained, m.p. 128°–130° (from ethanol).

EXAMPLE 3

3-Allyl-2,3,4,5-tetrahydro-11-phenyl-1H-[1,4]diazepino-[1,7-a]indole

[process (c)]

4 g 2,3,4,5-Tetrahydro-11-phenyl-1H-[1,4]diazepino[1,7-a]indole, 1.4 ml allyl bromide and 4.5 g potassium carbonate in 45 ml dimethylformamide are stirred for 2 hours at 110°. The mixture is poured onto water and extracted with ethyl acetate. The organic phase is dried and the solvent evaporated. The oily residue is chromatographed on 50 g silica gel using methylene chloride as eluant to give the title compound. M.p. of the hydrogen maleate 148°–150° (from ethanol/ether).

EXAMPLE 4

3-Cyclopropylmethyl-2,3,4,5-tetrahydro-11-phenyl-1H-[1,4]diazepino[1,7-a]indole

[process (c)]

A solution of 2.1 ml cyclopropanecarboxylic acid chloride in 25 ml chloroform is added to a boiling solution of 5.2 g 2,3,4,5-tetrahydro-11-1H-[1,4]diazaepino[1,7-a]indole and 4.2 ml triethyl amine. After 30 minutes 2N hydrochloric acid and water are added. The organic phase is dried and evaporated under reduced pressure, whereby the cyclopropanecarboxamide is obtained, m.p. 178°–180° (from ethanol). A solution of 2.35 ml sulphuric acid monohydrate in 15 ml tetrahydrofuran is added dropwise to a suspension of 3.34 9 lithium aluminium hydride in 35 ml tetrahydrofuran at 0°. The mixture is stirred at 0° for 15 minutes and then heated under reflux. A solution of 5.8 g 2,3,4,5-tetrahydro-11-phenyl-1H-[1,4]diazepino [1,7-a]indole-3-cyclopropanecarboxamide in 58 ml tetrahydrofuran is added dropwise. The mixture is stirred and heated under reflux for 3 ½ hours, cooled to 0° and treated with 12.8 ml saturated sodium sulfate solution. Thereafter 6.4 ml 30% sodium hydroxide solution are added and the mixture is further stirred for 1 hour at 35°. The precipitate is filtered and washed with ether, the filtrate is evaporated under reduced pressure to give the title compound. M.p. of the hydrochloride 225°–227° (from ethanol).

EXAMPLE 5

In analogous manner to that disclosed in Example 1, the following compounds of formua Ia are produced, wherein $R_3'$ is hydrogen:

| Ex. | $R_1$ | $R_2$ | $R_4$ | $R_5$ | $R_6$ | m.p. °C. |
|---|---|---|---|---|---|---|
| a | 8-Cl | H | H | H | H | 139–140 |
| b | 9-Cl | H | H | H | H | 114–115 |
| c | 8-F | H | H | H | H | 145–146 |
| d | 9-F | H | H | H | H | 143–145 |
| e | 8-OCH$_3$ | H | H | H | H | 237–239[2] |
| f | 9-OCH$_3$ | H | H | H | H | 203–205[1] |
| g | 8-CH$_3$ | H | H | H | H | 109–110 |
| h | 9-CH$_3$ | H | H | H | H | 212–214[2] |
| i | 8-CF$_3$ | H | H | H | H | 233–235[2] |
| j | H | p-Cl | H | H | H | 146–148 |
| k | H | m-Cl | H | H | H | 96–98 |
| l | H | o-Cl | H | H | H | 278–279[3] |
| m | 7-Cl | H | H | H | H | 111–112 |
| n | 10-Cl | H | H | H | H | 198–200[3] |
| o | H | H | H | H | CH$_3$ | 248–250[3] |
| p | H | H | H | CH$_3$ | H | 125–128[2] |
| q | H | H | H | CH$_3$ | CH$_3$ | 180–182[2] |
| r | H | H | CH$_3$ | H | H | 196–198[2] |
| s | H | H | CH$_3$ | H | CH$_3$ | 138[4] |
| t | H | H | CH$_3$ | CH$_3$ | CH$_3$ | 100–101[5] |

Example 6

3-Cyclopropylmethyl-2,3,4,5-tetrahydro-11-phenyl-1H-[1,4]diazepino[1,7-a]indole

[process (a)]

In manner analogous to that described in Example 1 and using 2,3-dihydro-3-cyclopropylmethyl-11-phenyl-1H-[1,4]diazepino[1,7-a]indol-4-(5H)-one as starting material the title compound is produced.

119 g of the title compound are dissolved in 600 ml abs. ethanol and cooled in an ice bath. 132 ml ethanolic HCl (3.4N) are added dropwise under stirring. The hydrochloride precipitates and after addition of 900 ml ether and stirring for 15 minutes the hydrochloride of the title compound is filtered off, m.p. 227°–228°.

The starting material may be obtained as follows:

3-Phenyl-1H-indol-2-ethanamine are reacted with cyclopropanecarboxylic acid chloride to give N-cyclopropylcarbonyl-3-phenyl-1H-indol-2-ethanamine, which is reduced with lithium aluminium hydride to N-cyclopropylmethyl-3-phenyl-1H-indol-2-ethanamine, which is reacted with chloracetyl chloride to give 2-chloro-N-cyclopropylmethyl-N-[2-(3-phenyl1H-indol-2-yl)ethyl]acetamide, m.p. 104°–106° (from ethanol/pentane).

A solution of 184.3 g 2-chloro-N-cyclopropylmethyl-N-[2-(3-phenyl-1H-indol-2-yl)ethyl]acetamide in 1843 ml methylene chloride is added dropwise under vigorous stirring to a suspension of 17.9 g N-benzyltributylammoniumbromide in 1843 ml methylene chloride and 921 ml 30% sodium hydroxide. The mixture is stirred for further 10 minutes and diluted with 1 l water. The organic phase is separated, washed with water, dried and evaporated to dryness. The residue is dissolved in 500 ml boiling ethanol, cooled and treated with 500 ml ether. The resulting cristalline precipitate is filtered off, washed with ethanol/äther (1:1) and then ether to give 2,3-dihydro-3-cyclopropylmethyl-11-phenyl-1H-[1,4]diazepino[1,7-a]indol-4(5H)-one, m.p. 149°–150°.

EXAMPLE 7

The following compounds of formula I are produced:

| Ex. | $R_1$ | $R_2$ | $R_3$ | $R_4$ | $R_5$ | $R_6$ | m.p. °C. | Analogous to Example |
|---|---|---|---|---|---|---|---|---|
| a | H | H | CH(CH$_3$)$_2$ | H | H | H | 229–232[2] | 3 |
| b | H | H | CH$_2$CH(CH$_3$)$_2$ | H | H | H | 211–223[3] | 1,3 |
| c | H | H | CH$_2$–cyclopropyl | H | H | H | 185–187[1] | 1,3 |
| d | H | H | CH$_2$–cyclopentyl | H | H | H | 115–117 | 1,3 |
| e | H | H | CH$_2$C(CH$_3$)=CH$_2$ | H | H | H | 223–228[3] | 3 |
| f | H | H | CH$_2$CH=CHCH$_3$ | H | H | H | 93–95 | 3 |

The compounds of the invention exhibit pharmacological activity and are therefore indicated for use as pharmaceuticals, e.g. for therapy. In particular, the compounds of the invention show antidepressant activity, as indicated by their central antiserotoninergic activity.

For example the compounds have a strong affinity for 5-HT$_2$ receptors in the rat frontal cortex [modified method of S.J. Peroutka and S. H. Snyder, Molec. Pharmacol. 16, 687 (1979). This test has been carried out as follows:

Fresh frontal cortex tissue from rat brain is homogenized in a 20 fold volume of Tris-HCl buffer (50 mM, pH 7.7, containing 4 mM $CaCl_2$, 10 μM pargyline, and 0.1% ascorbic acid), and centrifuged. The pellets are resuspended in a 25 fold volume of the same buffer, incubated for 15 min at 37° C., and recentrifuged. The pellets are frozen at −20° C. and resuspended in a 360 fold volume of the same buffer as above before use for the binding experiment. The composition of the assay mixtures (total volume =2 ml) is as follows: 50 mM Tris-HCl pH 7,7, 4 mM $CaCl_2$, 10 μM pargyline, 0.1% ascorbic acid, membranes corresponding to 5 mg of original tissue weight, and 1 nM $^3$H-spiperone. The assays for the determination of nonspecific binding additionally contain cinanserin in a concentration of 1 μM. To assess the potency of drugs in inhibiting the specific binding of $^3$H-spiperone to 5-HT$_2$-receptors (difference between total and nonspecific binding), the test compounds are added to give 5 to 9 different concentrations usually between 1 nM and 10 μM, each in duplicate. After incubation for 1 hour at 37° C., the assay mixtures are rapidly filtered through Whatman GF/B filters and washed twice with 5 ml of ice cold incubation buffer. $IC_{50}$ values (concentration of a test drug which inhibits specific binding of $^3$H-spiperone by 50%) are calculated by linear regression analysis from the Hill-plot. The $IC_{50}$ of the compounds of Examples 1, 2, 3 and 4 is 1 to 10 nM, the $IC_{50}$ of amitriptyline is 15 nM.

The compounds of the invention antagonize further L-5-hydroxytryptophan induced tremor in mice [modified method of R. Ortmann et al., Naunyn-Schmiedeberg's Arch. Pharmacol. 311, 185–192 (1980)]. The test was performed as follows:

Groups of 4 mice (female, 18–24 g, OF-1, SANDOZ, Basle) received 20 mg/kg i.p. clorgyline at time −45'. The test-drug (3.2, 10 and 32 mg/kg) was administered i.p. at time −30', followed by 15 mg/kg i.p. L-5-hydroxytryptophan 30' later, at time 0. The tremor was then scored on a 5-point basis at times +10', +20', +30', +40', +50' and +60'. The tremor was judged to be absent (0 points), intermittently present (1 point), present (2 points), present and strong (3 points) or present and extremely strong (4 points). For the 4 test mice over the 6 observation periods this gave a possible maximal score of 96 points. The observed scores were expressed as % of this maximum and compared with those of a control group which received saline instead of test-drug. The statistical significance of effects was estimated by comparing the total point score of each drugged mouse with the individual total scores of the control mice, using the Mann-Whitney U-test. The example 4 compound antagonizes tremor at 10 mg/kg i.p., dibenzepine at 10 mg/kg i.p.

The compounds of the invention reduce further the paradoxical sleep (PS) without rebound in the 48 h sleep EEG as e.g. amitriptyline on administration of 3.2–32 mg/kg p.o. to rats [H. Kleinlogel "EEG in Drug Research" ed. by Hermann, Gustav Fischer Verlag, Stuttgart, N.Y., 75–88 (1982)].

The compounds of the invention are therefore useful for the treatment of depression. For this use the exact dosage will, of course, vary depending on the compound employed, mode of administration and treatment desired. In general, satisfactory results are obtained when administered at a daily dosage of from about 0.5 to about 30 mg/kg animal body weight. For the larger mammals an indicated daily dosage is in the range from about 25 to about 500 mg of the compound conveniently administered in divided doses 2 to 4 times a day in unit dosage form containing for example from about 6 mg to about 250 mg of the compound or in sustained release form.

Furthermore the compounds of the invention show conflict reducing activity. For example, the frequency and duration of the ethological element "stretched attend posture" (SAP), indicative of an approachavoidance conflict, is determined after administration of 0.1 to 10 mg/kg p.o. of the compounds of the invention to male mice [H. P. Käsermann, Experientia 39 (1983), 681–682]. The test is performed as follows:

Groups of 8 male mice (LAC, 40–50 g, Bromfield Ltd., Newton Abbot GB) maintained under a reversed light-dark cycle, are treated orally with one of three doses of 0.1, 1.0 or 10 mg/kg of the test drug. 1 hour after administration mice were individually placed on a unknown, perforated, marked plastic platform and the behaviour was analyzed during a 2 minutes test period. Changes in frequency and duration of behavioural acts were assessed by individual comparisons between drug and control animals with the Mann-Whitney U-test. The compounds of the invention reduce stretched attend posture [SAP]in both frequency and duration. The reduction of the behavioural element SAP shows conflict reducing properties of these drugs in a non-social situation. The example 4 compound is active at 1 mg/kg p.o..

The compounds of the invention are therefore useful as conflict reducing agents e.g. as flanking medication in psychotherapeutic treatment and as anti-anxiety agents in the treatment of psychiatric disorders characterized by social withdrawal and anxiety. For this use the exact dosage will, of course, vary depending on the compound employed, mode of administration and treatment desired. In general, satisfactory results are obtained when administered at a daily dosage of from about 0.1 to about 10 mg/kg animal body weight. For the larger mammals an indicated daily dosage is in the range from about 20 to about 300 mg of the compound e.g. about 25 to about 300 mg conveniently administered in divided doses 2 to 4 times a day in unit dosage form containing for example from about 5 mg to about 150 mg of the compound or in sustained release form.

Furthermore the compounds of the invention exhibit neuroleptic activity, as indicated in standard tests, e.g. by an inhibition of locomotion in mice. In this test groups of 3 male mice (18–24 g, OF-1, Sandoz Basle) received 3.2, 10, 32, 100 and 320 mg p.o. of the test drug. 1 hour after drug administration the mice were observed individually and their locomotion compared with that of control. The locomotion is judged to be either unaffected, definitely more or less than controls, strongly more or less than controls, or completely inhibited. The $ED_{min}$ for the Example 5 j compound is 3.2 mg/kg p.o., the $ED_{min}$ of thioridazine is 10–32 mg/kg p.o.

The compounds of the invention bind further on $^3$H-spiperone binding sites in the brain [modified method of J. Leysen et al., Biochem. Pharmac. 27, 307 (1978)]. The test was performed as follows: fresh calf brain striatal tissue was homogenized in the 25 fold volume of Tris buffer (pH 7.4, 50 mM, 120 mM sodium chloride) and centrifuged. The pellets were suspended in the 22 fold volume of Tris buffer, incubated for 15 minutes at 37° C. and centrifuged. The pellets were suspended in the 300 fold volume of Tris buffer. The composition of the assay mixtures was as follows: 45 mM Tris buffer pH 7.7, 108 mM sodium chloride, membranes corresponding to 6 mg of original tissue weight, 0.1 nM $^3$H-spiperone, $5\times10^{-7}$M Cinanserin to eliminate the contribution of 5-HT$_2$ receptors and 1 μM unlabelled spiperone for the determination of non-specific binding. To determine the inhibition of the specific binding of $^3$H-spiperone the test drugs were added to give 5 to 9 different concentrations between 1 nM and 10 μM, each in duplicate. After incubation for 40 minutes at room temperature, the assay mixtures were rapidly filtered through Whatman GF/B filter, the filter washed twice with 5 ml of ice cold Tris buffer and scintillation-counted. The IC$_{50}$ values (concentration of a test drug which inhibits specific binding of $^3$H-spiperone by 50%) are determined by linear regression analysis. The IC$_{50}$ of the Example 5j compound is 137 nM, the IC$_{50}$ of thioridazine is 33 nM, the IC$_{50}$ of clozapine 990.

The compounds of the invention are therefore useful as neuroleptic agents in the treatment of e.g. psychotic disorders such as schizophrenia. For this use the exact dosage will, of course, vary depending on the compound employed, mode of administration and treatment desired. In general, satisfactory results are obtained when administered at a daily dosage of from about 1 to about 50 mg/kg animal body weight. For the larger mammals an indicated daily dosage is in the range from about 25 to about 600 mg of the compound conveniently administered in divided doses 2 to 4 times a day in unit dosage form containing for example from about 6 mg to about 300 mg of the compound or in sustained release form.

The example 4 compound is the preferred compound. The antidepressant indication is the preferred indication.

The compounds of the invention may be administered in similar manner to known standards for use in the same indication, e.g. amitriptyline in the antidepressant treatment and thioridazine in the antipsychotic treatment. The suitable daily dosage for a particular compound will depend on a number of factors such as its relative potency of activity. It has for example been determined that the preferred compound of the invention has a similar order of antidepressant activity to amitriptyline. It is therefore indicated that the compound may be administered at similar dosages than conventionally employed for amitriptyline.

The compounds of the invention may be administered in free base form or in pharmaceutically acceptable acid addition salt form. Such salts may be prepared in conventional manner and exhibit the same order of activity as the free base form. The present invention also provides a pharmaceutical composition comprising a compound of the invention in free base form or in salt form in association with a pharmaceutically acceptable diluent or carrier. Such compositions may be formulated in conventional manner. The compounds may be administered by any conventional route in particular enterally preferably orally e.g. in the form of tablets or capsules, or parenterally e.g. in form of injectable solutions or suspensions.

In one group of compounds of formula I R$_1$ and R$_2$ are each independently hydrogen, halogen of atomic number from 9 to 35, (C$_{1-4}$)alkyl, (C$_{1-4}$)alkoxy or trifluoromethyl, R$_3$ is hydrogen, (C$_{1-4}$)alkyl, (C$_{3-6}$)cycloalkyl(C$_{1-3}$)alkyl, (C$_{3-5}$)alkenyl or (C$_{3-5}$)alkynyl, R$_4$, R$_5$ and R$_6$ are each independently hydrogen or (C$_{1-4}$)alkyl, whereby at least one of R$_4$, R$_5$ and R$_6$ is hydrogen, and acid addition salts thereof.

In another group of compounds of formula I R$_1$ is hydrogen, halogen of atomic number from 9 to 35, (C$_{1-4}$)alkyl, (C$_{1-4}$)alkoxy or trifluoromethyl, R$_2$ is hydrogen or halogen of atomic number from 9 to 35, R$_3$ is hydrogen, (C$_{1-4}$)alkyl, (C$_{3-6}$)cycloalkyl(C$_{1-3}$)alkyl or (C$_{3-5}$)alkenyl, R$_4$, R$_5$ and R$_6$ are each independently hydrogen or (C$_{1-4}$)alkyl, and acid addition salts thereof.

In a first group of compounds R$_1$ is hydrogen.
In a second group of compounds R$_1$ is halogen.
In a third group of compounds R$_1$ is (C$_{1-4}$)alkyl.
In a fourth group of compounds R$_1$ is (C$_{1-4}$)alkoxy.
In a fifth group of compounds R$_1$ is trifluoromethyl.
In a sixth group of compounds R$_2$ is hydrogen.
In a seventh group of compounds R$_2$ is halogen.
In a eighth group of compounds R$_3$ is hydrogen.
In a ninth group of compounds R$_3$ is (C$_{1-4}$)alkyl.
In a tenth group of compounds R$_3$ is (C$_{3-6}$)cycloalkyl(C$_{1-3}$)alkyl.
In a eleventh group of compounds R$_3$ is (C$_{3-5}$)alkenyl.
In a twelfth group of compounds R$_4$ is hydrogen.
In a thirteenth group of compounds R$_4$ is (C$_{1-4}$)alkyl.
In a fourteenth group of compounds R$_5$ is hydrogen.
In a fifteenth group of compounds R$_5$ is (C$_{1-4}$)alkyl.
In a sixteenth group of compounds R$_6$ is hydrogen.
In a seventeenth group of compounds R$_6$ is (C$_{1-4}$)alkyl.

What we claim is:

1. A. compound of formula I

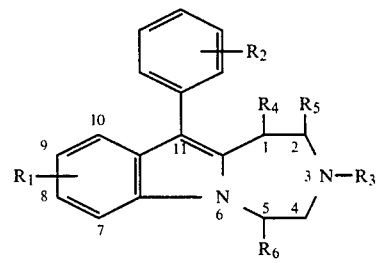

wherein
R$_1$ and R$_2$ are each, independently, hydrogen, halogen of atomic number from 9 to 35, (C$_{1-4}$)alkyl, (C$_{1-4}$)alkoxy or trifluoromethyl, R$_3$ is hydrogen, (C$_{1-4}$)alkyl, (C$_{3-6}$)cycloalkyl, (C$_{3-6}$)-cycloalkyl-(C$_{1-3}$)alkyl, (C$_{3-5}$)alkenyl or (C$_{3-5}$)alkynyl and R$_4$, R$_5$ and R$_6$ are each, independently, hydrogen or (C$_{1-4}$)alkyl, or a pharmaceutically acceptable acid addition salt thereof.

2. A compound of claim 1 wherein R$_1$ and R$_2$ are each independently hydrogen, halogen of atomic number from 9 to 35, (C$_{1-4}$)alkyl, (C$_{1-4}$)alkoxy or trifluoromethyl, R$_3$ is hydrogen, (C$_{1-4}$)alkyl, (C$_{3-6}$)cycloalkyl(C$_{1-3}$)alkyl, (C$_{3-5}$)alkenyl or (C$_{3-5}$)alkynyl and R$_4$, R$_5$ and R$_6$ are each independently hydrogen or (C$_{1-4}$)alkyl, whereby at least one of R$_4$, R$_5$ and R$_6$ is hydrogen, or a pharmaceutically acceptable acid addition salt thereof.

3. A compound of claim 1 wherein R is hydrogen, halogen of atomic number from 9 to 35, (C$_{1-4}$)alkyl, (C$_{1-4}$)alkoxy or trifluoromethyl, R$_2$ is hydrogen or halogen of atomic number from 9 to 35, R$_3$ is hydrogen, (C$_{1-4}$)alkyl, (C$_{3-6}$)cycloalkyl(C$_{1-3}$)alkyl or (C$_{3-5}$)alkenyl, and R$_4$, R$_5$ and R$_6$ are each independently hydrogen or (C$_{1-4}$)-alkyl, or a pharmaceutically acceptable acid addition salt thereof.

4. A compound of claim 1 which is 3-cyclopropylmethyl-2,3,4,5-tetrahydro-11-phenyl-1H-[1,4]diazepino[1,7-a]indole, or a pharmaceutically acceptable acid addition salt thereof.

5. A pharmaceutical composition useful in treating depression, schizophrenia, social withdrawal or anxiety comprising a pharmaceutically acceptable carrier or diluent and a therapeutically effective amount of a compound of claim 1, or a pharmaceutically acceptable acid addition salt thereof.

6. A method of treating depression which comprises administering a therapeutically effective amount of a compound of claim 1, or a pharmaceutically acceptable acid addition salt thereof, to a subject in need of such treatment.

7. A method of treating schizophrenia which comprises administering a therapeutically effective amount of a compound of claim 1, or a pharmaceutically acceptable acid addition salt thereof, to a subject in need of such treatment.

8. A method of treating social withdrawal which comprises administering a therapeutically effective amount of a compound of claim 1, or a pharmaceutically acceptable acid addition salt thereof, to a subject in need of such treatment.

9. A method of treating anxiety which comprises administering a therapeutically effective amount of a compound of claim 1, or a pharmaceutically acceptable acid addition salt thereof, to a subject in need of such treatment.

* * * * *